United States Patent
Lallier

(10) Patent No.: US 9,232,789 B2
(45) Date of Patent: Jan. 12, 2016

(54) BIOSTATIC NEUTRALIZING COMPOSITION FOR AQUEOUS FLUIDS

(75) Inventor: Jean-Pierre Lallier, Saint Bonnet de Mure (FR)

(73) Assignee: ARKEMA FRANCE, Colombes (FR)

( * ) Notice: Subject to any disclaimer, the term of this patent is extended or adjusted under 35 U.S.C. 154(b) by 123 days.

(21) Appl. No.: 13/822,174

(22) PCT Filed: Sep. 27, 2011

(86) PCT No.: PCT/FR2011/052252
§ 371 (c)(1),
(2), (4) Date: Apr. 12, 2013

(87) PCT Pub. No.: WO2012/045958
PCT Pub. Date: Apr. 12, 2012

(65) Prior Publication Data
US 2013/0217780 A1    Aug. 22, 2013

(30) Foreign Application Priority Data

Sep. 27, 2010 (FR) ...................... 10 57744

(51) Int. Cl.
*A01N 33/08* (2006.01)
*C02F 1/50* (2006.01)
*C02F 1/66* (2006.01)

(52) U.S. Cl.
CPC . *A01N 33/08* (2013.01); *C02F 1/50* (2013.01); *C02F 1/66* (2013.01)

(58) Field of Classification Search
CPC ....... A01N 33/02; A01N 33/04; A01N 33/08; C02F 1/50; C02F 1/66

USPC ...................... 106/15.05, 18, 18.32
See application file for complete search history.

(56) References Cited

U.S. PATENT DOCUMENTS 7,604,751 B2 * 10/2009 Yoneda et al. .................. 216/88

FOREIGN PATENT DOCUMENTS

| WO | 03/011347 A1 | 2/2003 |
| WO | WO 2006115393 A1 * | 11/2006 |
| WO | WO 2006127885 A1 * | 11/2006 |
| WO | WO 2010048139 A2 * | 4/2010 |

OTHER PUBLICATIONS

Derwent-Acc-No. 2010-J03464, abstract of Chinese Patent Specification No. CN 101738879A (Jun. 2010).*
Derwent-Acc-No. 2010-P32368, abstract of Chinese Patent Specification No. CN 101864589 A (Oct. 2010).*
Derwent-Acc-No. 2011-D00250, abstract of Chinese Patent Specification No. CN 101955840A (Jan. 2011).*
Derwent-Acc-No. 2009-G00995, abstract of Chinese Patent Specification No. CN 101368273 A (Feb. 2009).*
International Search Report received in PCT/FR2011/052252, mailed Feb. 2, 2012. English translation provided.

* cited by examiner

*Primary Examiner* — Anthony J Green
(74) *Attorney, Agent, or Firm* — Smith, Gambrell & Russell, LLP

(57) ABSTRACT

The invention relates to a biostatic neutralizing composition for aqueous fluids, including two amines, one of which is dihydroxyethylamine. The invention also relates to the use of such a composition as a biostatic neutralizing additive for industrial aqueous fluids. The invention further relates to the industrial aqueous fluids containing such a composition.

33 Claims, 1 Drawing Sheet

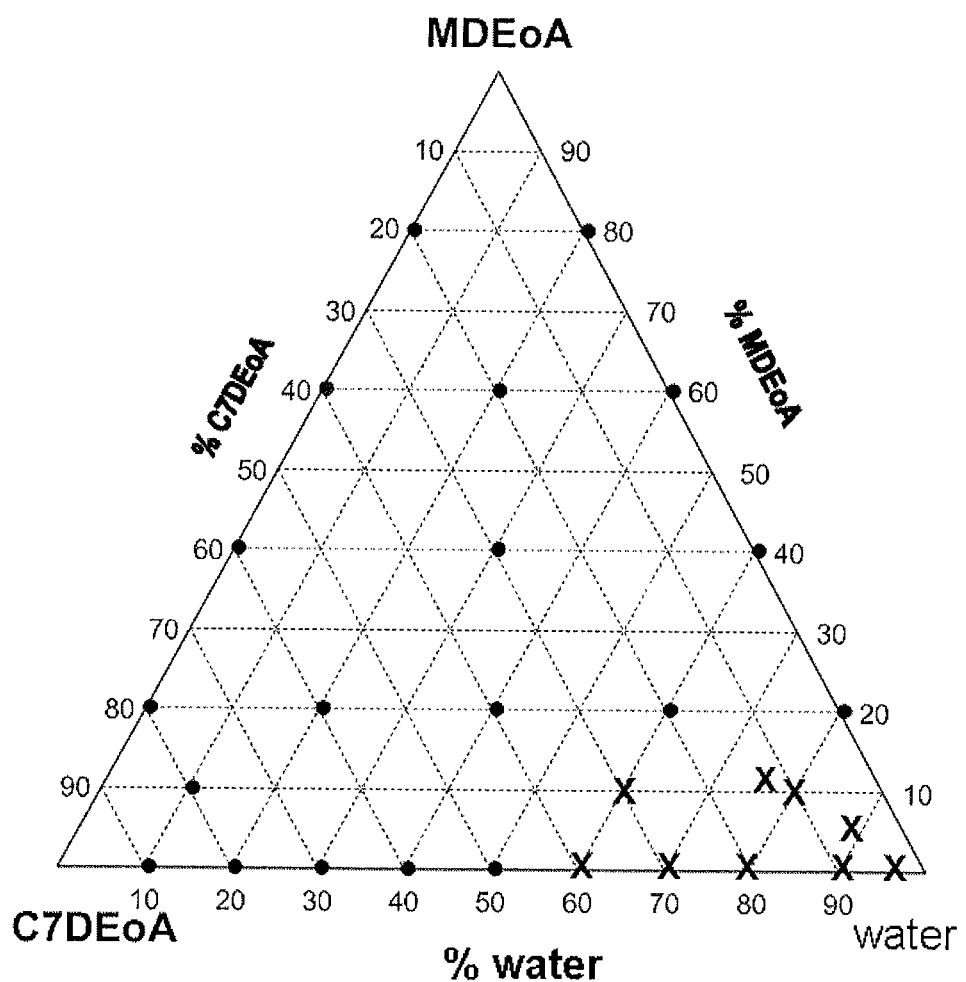

BIOSTATIC NEUTRALIZING COMPOSITION FOR AQUEOUS FLUIDS

The present invention relates to a composition, more specifically a composition based on amines, enabling the neutralization of aqueous fluids, such as aqueous dispersions of mineral fillers, metal working fluids, and others, while limiting or preventing bacterial growth and proliferation in said aqueous fluids.

With the ever expanding development of paints, inks, varnishes and other coatings that are solvent-free or that have a reduced content of solvent, it is necessary to be able to disperse mineral fillers in water. The technique of dispersing mineral fillers in water is a technique that is today well known, but the dispersions that result therefrom can pose some problems.

Indeed, in aqueous paints, such as acrylic-based latex paints, a pH adjustment is generally necessary in order to stabilize the latex. This adjustment is referred to as neutralization. Furthermore, when a pigment concentrate is diluted in a white paint or white base, whether it be aqueous or solvent-based, it is also necessary to neutralize these pigment concentrates.

In the paper industry, it is also necessary to neutralize the aqueous dispersions of mineral fillers intended for coating paper, due to the acidity of the dispersion agents used, such as for example the dispersion agents Coatex® P90 from Coatex or Dysperbyk® 191 or BYK® 192 from BYK-Chemie GmbH, or Orotan™ 850ER from Rohm & Haas.

As neutralizing agent, use is commonly made of ammonia, sodium hydroxide, dimethylamine, monoethanolamine, diethanolamine and N-methylethanolamine. Other neutralizing agents that have arrived more recently on the market are alkylalkanolamines, among which mention may be made of 2-amino-2-methyl-1-propanol (CAS No. 124-68-5), sold under the trademark AMP® at 90% or 95% in water under the names AMP® 90 and AMP® 95 respectively, by Angus, or else N-n-butyl-N-(2-hydroxylethyl)amine and N-(1-methylpropyl)-N-(2-hydroxyethyl)amine, sold by Arkema under the name Alpamine™ N41.

These neutralizing agents, which are generally mineral or organic bases, commonly used today, have the advantage of being perfectly soluble in water and enable an effective neutralization of the aqueous dispersions of mineral fillers.

Typically, the pH of a latex is ideally adjusted to a value between 8 and 10, preferably between 8.5 and 9.5 when the neutralizing amine (adjusting amine) is added in a proportion of from 0.1% to 0.5% by weight, preferably from 0.1% to 0.3%, more preferably from 0.1% to 0.2%. In pigment concentrates, the amount of codispersant amine is, preferably, kept below 3.5% by weight.

However, these aqueous dispersions may become unstable, especially due to bacterial growth and the proliferation of bacteria which may occur within them. The expression "bacterial growth and bacterial proliferation" is understood, within the meaning of the present invention, to mean the growth and proliferation of bacteria, the growth and proliferation of mycobacteria, fungal growth and proliferation, and in general any growth and proliferation of living organisms, capable of destabilizing the aqueous fluids, of coloring them, of giving them an unpleasant odor, of thickening them, of rendering them non-homogeneous, and more generally of rendering them unsuitable for the uses thereof for which they were conceived.

Therefore, the addition to these aqueous fluids of one or more biostatic agents (that prevent the proliferation of bacteria if they have appeared) and/or biocidal agents (agents that "kill" bacteria, thus preventing the appearance of bacteria) is recommended. The biostatic and/or biocidal agents commonly used today are typically biocides based on formaldehyde, glutaraldehyde and/or isothiazolone, for example those sold by Thor under the name Acticide®.

These biostatic and/or biocidal agents are perfectly soluble in aqueous media and perfectly compatible with the neutralizing agents set out above.

However, some of these biostatic and/or biocidal agents may lead to pH stability problems, and some are now considered to be harmful or dangerous for the environment; the environmental regulations in force or to come require their partial or complete replacement by compounds that are not harmful and not dangerous for the environment.

In U.S. Pat. No. 4,925,582, it is indicated that certain amines, which can be used in industrial hydraulic fluids and/or as neutralizing agents, exhibit antibacterial properties, thus making it possible to reduce the effective amount of environmentally harmful biocides.

Although these amines can be considered to be sufficiently compatible with aqueous fluids, soluble in aqueous media and sufficiently basic to enable the neutralization of the aqueous fluids when necessary, these amines do not however exhibit a satisfactory, or even sufficient, antimicrobial action.

There therefore remains a need for additives for aqueous fluids that exhibit both a neutralizing action and a biostatic action, that is to say agents that prevent or limit (myco) bacterial and/or fungal proliferation.

BRIEF DESCRIPTION OF THE DRAWING

Further features and advantages of the invention can be ascertained from the following detailed description that is provided in connection with the drawing described below:

FIG. 1 illustrates a graphical representation of the solubility of compositions according to one embodiment of the present invention.

Thus, a first objective of the invention is to provide novel biostatic neutralizing agents in aqueous fluids which are effective, both as regards the adjustment of the pH of said aqueous fluids and as regards (myco)bacterial and/or fungal anti-proliferation within said aqueous fluids, and which are in addition perfectly compatible with said aqueous fluids.

Yet other objectives will appear in the description of the invention which follows.

The Applicant has now discovered that these objectives may be achieved completely or partly owing to the compositions according to the present invention.

Thus, a first subject of the present invention is a biostatic neutralizing composition for aqueous fluids comprising at least one organic or mineral base (B) and at least one amine of formula (2):

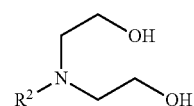

(2)

wherein $R^2$ represents a linear or branched hydrocarbon-based radical, preferably a linear or branched alkyl radical, having 7, 8, 9, 10, 11 or 12 carbon atoms.

The base (B) may be of any type known per se, and, as non-limiting examples, the mineral bases may advantageously be chosen from alkali metal hydroxides or alkaline-earth metal hydroxides, in particular from sodium, potassium or calcium hydroxide, and nitrogenous bases, preferably bases comprising at least one amine group, more preferably 1 amine group.

As a variant, the base (B) may be an organic base, such as those commonly used by a person skilled in the art, in particular nitrogenous bases, for example ammonium hydroxide, and more particularly the bases comprising at least one amine group, more preferably 1 amine group.

According to one preferred aspect of the present invention, the base (B) is an organic base, quite preferably the base (B) is an amine of low molecular weight, that is to say, within the meaning of the present invention, an amine having a total number of carbon atoms of less than or equal to 10, preferably a total number of carbon atoms of less than or equal to 9. For the requirements of the invention, cyclic amines are not preferred.

The amines of low molecular weight are preferably monoamines and may be primary, secondary or tertiary amines. The nitrogen atom may be substituted by 1 hydroxyalkyl radical or 2 hydroxyalkyl radicals, or even 3 hydroxyalkyl radicals, preferably by 1 or 2, or even 3 hydroxyethyl radicals, more preferably 1 or 2 hydroxyethyl radicals, more preferably still 2 hydroxyethyl radicals.

More preferably still, the base (B) is an amine of formula (1):

wherein:
either $R^1$ represents a linear or branched hydrocarbon-based radical, preferably a linear or branched alkyl radical, having 1, 2, 3, 4, 5 or 6 carbon atoms, and $R^a$ and $R^b$ each represent the radical —(CH$_2$—CH$_2$)—OH, or $R^1$ represents a hydrogen atom and $R^a$ represents a hydrogen atom and $R^b$ represents the radical —(CH$_2$—CH$_2$)—OH.

In one particularly preferred embodiment, a subject of the present invention is a biostatic neutralizing composition for aqueous fluids comprising at least one amine having a total number of carbon atoms of less than 10, preferably of less than 9, preferably at least one amine of formula (1) and at least one amine of formula (2):

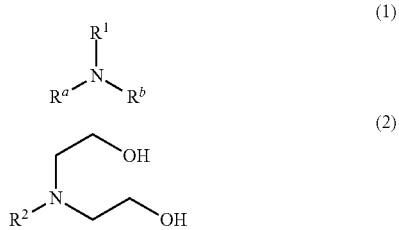

in which $R^a$, $R^b$, $R^1$ and $R^2$ are as defined previously.

The expression "neutralizing composition" is understood to mean a composition capable of neutralizing an acidic aqueous fluid, or else capable of adjusting the pH of an acidic aqueous fluid.

The expression "biostatic composition" is understood to mean a composition capable of preventing or at the very least limiting bacterial, mycobacterial and/or fungal proliferation of an aqueous fluid.

The expression "aqueous fluid" is understood to mean any type of industrial aqueous fluid, and in particular, as non-limiting examples, white bases of aqueous or aqueous-organic paints, aqueous pigment concentrates, aqueous dispersions of mineral fillers, metal working fluids, abrasive fluids for polishing glass (mirrors) and others.

The amines of formula (1) are known in themselves and are either commercially available or easily prepared from procedures that are known or readily accessible to a person skilled in the art in patent literature, scientific articles, scientific works, Chemical Abstracts or else on the Internet.

Among the amines of formula (1), within the context of the present invention, butylamine, hexylamine, (2-ethyl)hexylamine, monoethanolamine (MEA), N-(n-butyl)-N-hydroxy-ethylamine, N-(sec-butyl)-N-hydroxy-ethylamine, methyldiethanolamine (MDEoA), ethyldiethanolamine (EDEoA), propyldiethanolamine (PrDEoA), butyldiethanolamine (BDEoA), pentyldiethanolamine (PDEoA) and hexyldiethanolamine (HDEoA) are very particularly preferred, and very particularly preferably, the amine of formula (1) is chosen from monoethanolamine (MEoA), (2-ethyl)hexylamine and methyldiethanolamine (MDEoA).

The amines of formula (2) are known in themselves and are either commercially available or prepared easily from procedures that are known or readily accessible to a person skilled in the art in patent literature, scientific articles, scientific works, Chemical Abstracts or else on the Internet.

The amines of formula (2) may, for example, advantageously be obtained by reductive amination of a ketone or of an aldehyde by a primary amine or a primary hydroxyalkylamine, as described in international application PCT/FR2010/051299.

Among the amines of formula (2), within the context of the present invention, n-heptyldiethanolamine (C$_7$DEoA), n-octyldiethanolamine (C$_8$DEoA), 2-(ethyl)hexyldiethanolamine (C$_{2-6}$DEoA), n-decyldiethanolamine (C$_{10}$DEoA), n-undecyldiethanolamine (C$_{11}$DEoA) and n-dodecyldiethanolamine (C$_{12}$DEoA) are very particularly preferred. Very particularly preferably, the amine of formula (2) is n-heptyldiethanolamine (C$_7$DEoA).

According to one preferred embodiment of the present invention, the biostatic neutralizing composition comprises:
a) at least one mineral or organic base, preferably an organic base, and more preferably an amine-containing base, chosen from sodium hydroxide, potassium hydroxide, calcium hydroxide, aqueous ammonia, monoethanolamine (MEoA), (2-ethyl)hexylamine and methyldiethanolamine (MDEoA); and
b) at least one second amine of formula (2), preferably n-heptyldiethanolamine (C$_7$DEoA).

Compositions comprising monoethanolamine (MEoA) and n-heptyldiethanolamine (C$_7$DEoA) or compositions comprising methyldiethanolamine (MDEoA) and n-heptyldiethanolamine (C$_7$DEoA) are very particularly preferred.

In the compositions according to the present invention, the base (B)/amine (2) molar ratio, and in particular the amine (1)/amine (2) molar ratio, is generally between 1:99 and 99:1, preferably between 1:9 and 9:1. The molar ratio defined here generally depends on the nature of the aqueous fluid, on its degree of acidity, on the desired biostatic effect, on the temperature, and others. This molar ratio will be able to be optimized easily by a person skilled in the art.

According to one very particularly preferred embodiment, this molar ratio is advantageously between 1.5 and 3.

In practice, and especially when the base (B) is an amine of low molecular, the compositions according to the invention comprise from 40% to 99% by weight of at least one amine of low molecular weight and from 1% to 60% by weight of at least one amine (2), relative to the total weight of the composition.

According to another preferred aspect, these percentages range respectively from 50% to 80% by weight for the amine of low molecular weight and from 20% to 50% by weight for the amine (2) and more preferably from 60% to 80% by weight, and from 20% to 40% by weight respectively.

The amines of formula (2) possess quite advantageous biostatic properties, but are only weakly soluble or are insoluble in water and have neutralizing properties that are usually insufficient. The bases (B), and in particular the amines of formula (1), on the other hand are soluble in water and have a perfectly satisfactory neutralizing capacity.

The Applicant has now discovered, unexpectedly, that the combination of at least one base (B), preferably at least one amine of formula (1), with at least one amine of formula (2) gives the composition highly advantageous properties, and in particular very good neutralizing properties, very good biostatic properties, and also an excellent solubility in water.

Without wishing to be tied to the theory, the base (B), and in particular the amine of formula (1), acts as a co-solvent in water for the amine of formula (2).

Thus, the biostatic neutralizing compositions according to the invention have the very great advantage of making available to the final user a composition that is homogeneous, stable over time, and miscible in water, and that therefore requires only a single one-off addition of a solution to an aqueous fluid in order to be able both to adjust its pH and limit, or even prevent, bacterial proliferation within it.

Another advantage linked to the biostatic neutralizing compositions according to the invention is their dispersing power, or more precisely their co-dispersing power, when said compositions are used in aqueous dispersions of mineral fillers.

The compositions according to the present invention may be in concentrated form or diluted in water or in a water-soluble organic solvent or else in an aqueous-organic solvent, in any proportions, depending on the envisaged use.

The compositions according to the present invention may in addition comprise one or more additives commonly used in the envisaged fields of application. Among the additives that may be added to the compositions according to the present invention, mention may be made, as non-limiting examples, of co-solvents, surfactants, colorants, stabilizers, mineral or organic bases, biocides, UV stabilizers, and others.

According to a second aspect, the present invention relates to the use, as a biostatic neutralizing additive, of a composition comprising at least one base, preferably at least one amine of low molecular weight, more preferably at least one amine of formula (1), and at least one amine of formula (2) as described previously for an industrial aqueous fluid.

The biostatic and neutralizing effect of the industrial aqueous fluid is obtained by simple introduction and optional mixing into said industrial aqueous fluid of an effective amount of a composition according to the present invention.

The expression "effective amount" is understood, in the preceding paragraph, to mean an amount generally of between 0.0001% and 10% by weight of biostatic neutralizing composition relative to the total weight of the industrial aqueous fluid, preferably between 0.001% and 5% by weight. However, this amount depends on the envisaged application and on the desired effect. Thus, in general, this amount may be between 0.001% and 1%, preferably between 0.003% and 0.5% by weight, for example around 400 ppm by weight in the case of aqueous dispersions of mineral fillers; in the case of aqueous metal working solutions, this amount may be between 3% and 5% by weight.

Owing to their neutralizing, biostatic, water-soluble and co-dispersing capacities, the compositions according to the present invention find particularly suitable uses in industrial fluids of any type, such as for example those described above.

According to yet another aspect, the present invention relates to an industrial fluid comprising at least one biostatic neutralizing composition according to the present invention, the amount of said composition in said industrial fluid being as indicated previously.

The following examples illustrate the present invention without however limiting the scope thereof. In these examples, the parts and the percentages are by weight, unless otherwise indicated.

EXAMPLE 1

Test of Neutralization

The neutralizing capacity is evaluated by determining the weight of amine (in grams) necessary for neutralizing 100 g of oleic acid. In this example, the neutralizing capacities of the following products are compared:

Amine (1) alone: monoethanolamine (MEoA);

Amine (2) alone: n-heptyldiethanolamine ($C_7$DEoA);

Mixture of amine (1)+amine (2): 70% by weight of MEoA+30% by weight of $C_7$DEoA.

The results are presented in table 1 below:

TABLE 1

| | Amount necessary for neutralizing 100 g of oleic acid (g) |
|---|---|
| MEoA | 6.8 |
| $C_7$DEoA | 36 |
| MEoA (70%) + $C_7$DEoA (30%) | 8.8 |

Despite an observed neutralizing capacity that is much lower for $C_7$DEoA, it is observed that the mixture of MEoA (70%)+$C_7$DEoA (30%) retains a very good neutralizing capacity owing to the provision of MEoA.

EXAMPLE 2

Test of Solubility in Water

In this example, the following two amines are considered:

Amine (1) alone: methyldiethanolamine (MDEoA);

Amine (2) alone: n-heptyldiethanolamine ($C_7$DEoA).

The appended FIG. 1 represents a ternary phase diagram between these 2 amines and water. The percentages are expressed by weight. The miscible mixtures are denoted by points (●), the immiscible mixtures are denoted by crosses (X).

The $C_7$DEoA/water binary mixture is not miscible in all proportions. There is immiscibility when the $C_7$DEoA is found in an amount of greater than 50%. In the area of immiscibility (amount of $C_7$DEoA greater than 50%), the MDEoA acts as a coupling agent (co-solvent) when it is present in a content of greater than 15%.

EXAMPLE 3

Test of Bacterial Proliferation

A test is carried out in order to evaluate the bactericidal and/or bacteriostatic activity of a sample of the composition of the invention, according to the standard NF EN 1040 (April 2006).

A sample of a composition as it is (maximum concentration of the test: 80%) and/or diluted with water is added to a test suspension of bacteria (*Pseudomonas aeruginosa* and *Staphylococcus aureus*). The mixture is maintained at 20° C. for 5 minutes.

An aliquote portion is removed at the end of this contact time; the bactericidal and/or bacteriostatic activity in this withdrawal is immediately neutralized or suppressed according to a validated method. The method used preferably is the dilution-neutralization method. Filtration over a membrane is used when it is not possible to find a suitable neutralizer.

The surviving bacteria in each sample are counted, which makes it possible to calculate the degree of reduction, denoted by "+" (low degree of reduction) to "++++" (high degree of reduction) in table 2 below:

TABLE 2

| Composition | Degree of reduction |
| --- | --- |
| MEoA | + |
| C$_7$DEoA | ++++ |
| MEoA (70%) + C$_7$DEoA (30%) | +++ |
| MEoA (90%) + C$_7$DEoA (10%) | ++ |

The invention claimed is:

1. A biostatic neutralizing composition for aqueous fluids, comprising at least one amine of formula (1) and at least one amine of formula (2):

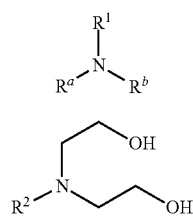

formula (1) and formula (2), wherein:
either $R^1$ represents a linear or branched hydrocarbon-based radical having 1, 2, 3, 4, 5 or 6 carbon atoms, and $R^a$ and $R^b$ each represent the radical —(CH$_2$—CH$_2$)—OH,
or $R^1$ represents a hydrogen atom and $R^a$ represents a hydrogen atom and $R^b$ represents the radical —(CH$_2$—CH$_2$)—OH,
and, in both the above cases, $R^2$ represents a linear or branched hydrocarbon-based radical having 7, 8, 9, 10, 11 or 12 carbon atoms.

2. The composition of claim 1, wherein the amine of formula (1) is selected from the group consisting of monoethanolamine (MEA), methyldiethanolamine (MDEoA), ethyldiethanolamine (EDEoA), propyldiethanolamine (PrDEoA), butyldiethanolamine (BDEoA), pentyldiethanolamine (PDEoA), and hexyldiethanolamine (HDEoA).

3. The composition of claim 1, wherein the amine of formula (2) is selected from the group consisting of n-heptyldiethanolamine (C$_7$DEoA), n-octyldiethanolamine (C$_8$DEoA), 2-(ethyl)hexyldiethanolamine (C$_{2-6}$DEoA), n-decyldiethanolamine (C$_{10}$DEoA), n-undecyldiethanolamine (C$_{11}$DEoA), and n-dodecyldiethanolamine (C$_{12}$DEoA).

4. The composition of claim 1, comprising at least one first amine selected from the group consisting of monoethanolamine (MEA) and methyldiethanolamine (MDEoA) and at least one second amine which is n-heptyldiethanolamine (C$_7$DEoA).

5. The composition of claim 1, comprising monoethanolamine (MEA) and n-heptyldiethanolamine (C$_7$DEoA) or methyldiethanolamine (MDEoA) and n-heptyldiethanolamine (C$_7$DEoA).

6. The composition of claim 1, in concentrated form or diluted in water or in a water-soluble organic solvent or else in an aqueous-organic solvent, in any proportions.

7. The composition of claim 1, wherein $R^1$ is a linear or branched alkyl radical.

8. The composition of claim 1, wherein $R^2$ is a linear or branched alkyl radical.

9. The composition of claim 2, wherein the amine of formula (1) is monoethanolamine (MEA) or methyldiethanolamine (MDEoA).

10. The composition of claim 3, wherein the amine of formula (2) is n-heptyldiethanolamine (C$_7$DEoA).

11. The composition of claim 1, wherein the amine (1) is present in an amount of about 60% to 80% by weight and the amine (2) is present in an amount of about 20% to 40% by weight, relative to the total weight of the composition.

12. The composition of claim 1, comprising an amine (1)/amine (2) molar ratio between 1:9 and 9:1.

13. A method for neutralizing an industrial aqueous fluid and limiting or preventing bacterial growth and proliferation in the aqueous fluid, comprising:
introducing, as a biostatic neutralizing additive, the composition of claim 1 into the aqueous fluid.

14. The method as claimed in claim 13, wherein the industrial aqueous fluid is an aqueous or aqueous-organic white paint base, an aqueous pigment concentrate, an aqueous dispersion of mineral fillers, or a metal working fluid.

15. An industrial aqueous fluid comprising at least one biostatic neutralizing composition as claimed in claim 1.

16. The fluid as claimed in claim 15, comprising between 0.0001 and 10% by weight of the at least one biostatic neutralizing composition.

17. The industrial aqueous fluid as claimed in claim 15, which is an aqueous or aqueous-organic white paint base, an aqueous pigment concentrate, an aqueous dispersion of mineral fillers, or a metal working fluid.

18. The fluid of claim 16, wherein the at least one biostatic neutralizing composition is present in an amount between 0.001% and 5% by weight.

19. A method for neutralizing an industrial aqueous fluid and limiting or preventing bacterial growth and proliferation in the aqueous fluid, comprising:

introducing, as a biostatic neutralizing additive, a composition comprising at least one organic or mineral base (B) and at least one amine of formula (2):

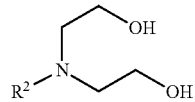
(2)

wherein $R^2$ represents a linear or branched hydrocarbon-based radical having 7, 8, 9, 10, 11 or 12 carbon atoms, into the aqueous fluid.

20. The method of claim 19, wherein the composition comprises a base (B)/amine (2) molar ratio between 1:9 and 9:1.

21. The method of claim 19, wherein $R^2$ is a linear or branched alkyl radical.

22. The method of claim 19, wherein the base (B) is an amine having a total number of carbon atoms of less than or equal to 10.

23. The method of claim 22, wherein the total number of carbon atoms is less than or equal to 9.

24. The method of claim 22, wherein the amine comprises 1, 2, or 3 hydroxyalkyl radicals.

25. The method of claim 22, wherein the amine comprises 1, 2, or 3 hydroxyethyl radicals.

26. The method of claim 19, wherein the base (B) is present in an amount of about 60% to 80% by weight and the amine (2) is present in an amount of about 20% to 40% by weight, relative to the total weight of the composition.

27. The method of claim 19, wherein the base (B) is an organic base.

28. The method of claim 19, wherein the base (B) is selected from the group consisting of alkali metal hydroxides, alkaline-earth metal hydroxides, and nitrogenous bases.

29. The method of claim 28, wherein the nitrogenous bases comprise at least one amine group.

30. The method of claim 29, wherein the nitrogenous bases have one amine group.

31. A biostatic neutralizing composition for aqueous fluids, comprising: at least one organic or mineral base (B) and at least one amine of formula (2):

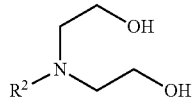
(2)

wherein $R^2$ represents a linear or branched hydrocarbon-based radical having 7, 8, 9, 10, 11 or 12 carbon atoms, and the base (B) is present in an amount of about 60% to 80% by weight and the amine (2) is present in an amount of about 20% to 40% by weight, relative to the total weight of the composition.

32. An industrial aqueous fluid, comprising:
at least one biostatic neutralizing composition comprising at least one organic or mineral base (B) and at least one amine of formula (2):

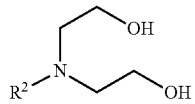
(2)

wherein $R^2$ represents a linear or branched hydrocarbon-based radical having 7, 8, 9, 10, 11 or 12 carbon atoms, and wherein the at least one biostatic neutralizing composition is present in an amount of 0.0001 to 10% by weight.

33. An industrial aqueous fluid including an aqueous or aqueous-organic white paint base, an aqueous pigment concentrate, an aqueous dispersion of mineral fillers, or a metal working fluid, comprising:
at least one biostatic neutralizing composition comprising at least one organic or mineral base (B) and at least one amine of formula (2):

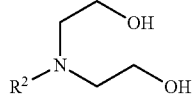
(2)

wherein $R^2$ represents a linear or branched hydrocarbon-based radical having 7, 8, 9, 10, 11 or 12 carbon atoms.

* * * * *